(12) United States Patent
Ueno

(10) Patent No.: US 7,033,604 B2
(45) Date of Patent: Apr. 25, 2006

(54) COMPOSITION FOR TOPICAL ADMINISTRATION

(75) Inventor: Ryuji Ueno, Potomac, MD (US)

(73) Assignee: Sucampo AG, Zug (CH)

( * ) Notice: Subject to any disclaimer, the term of this patent is extended or adjusted under 35 U.S.C. 154(b) by 61 days.

(21) Appl. No.: 10/187,013

(22) Filed: Jul. 2, 2002

(65) Prior Publication Data

US 2003/0044452 A1    Mar. 6, 2003

Related U.S. Application Data

(60) Provisional application No. 60/303,148, filed on Jul. 6, 2001.

(51) Int. Cl.
*A61F 2/00* (2006.01)
*A61K 31/44* (2006.01)
*A61K 31/47* (2006.01)

(52) U.S. Cl. .................... 424/427; 514/291; 514/312; 514/772; 424/401

(58) Field of Classification Search .............. 514/291, 514/312, 772; 424/401, 451, 427
See application file for complete search history.

(56) References Cited

U.S. PATENT DOCUMENTS

| | | | |
|---|---|---|---|
| 5,348,966 A * | 9/1994 | Starzl et al. ............... 514/326 |
| 5,385,907 A * | 1/1995 | Asakura et al. ............ 514/291 |
| 5,474,764 A * | 12/1995 | Patel et al. ............. 424/78.04 |
| 5,514,686 A * | 5/1996 | Mochizuki et al. ......... 514/297 |
| 5,880,101 A * | 3/1999 | Stankov ..................... 514/29 |
| 5,885,601 A * | 3/1999 | Sokal ........................ 424/405 |
| 5,912,255 A * | 6/1999 | Bussell ...................... 514/311 |
| 5,939,427 A * | 8/1999 | Kagayama et al. ......... 514/291 |
| 6,017,554 A * | 1/2000 | Ratcliff ....................... 424/422 |
| 6,087,358 A * | 7/2000 | Baker et al. ............. 514/230.5 |
| 6,140,355 A * | 10/2000 | Egidio et al. .............. 514/394 |
| 6,174,859 B1 * | 1/2001 | Lezdey et al. ................ 514/12 |
| 6,191,143 B1 * | 2/2001 | Watts et al. .................. 514/312 |
| 6,248,776 B1 | 6/2001 | Harris |
| 6,312,715 B1 | 11/2001 | Cantor et al. |
| 6,359,016 B1 * | 3/2002 | Singh et al. ............ 514/772.4 |
| 6,475,518 B1 * | 11/2002 | Baumgart et al. .......... 424/451 |
| 2003/0044452 A1 | 3/2003 | Ueno |
| 2003/0114416 A1 * | 6/2003 | Pulaski et al. ................ 514/54 |
| 2004/0019054 A1 * | 1/2004 | Roark ........................ 514/248 |

FOREIGN PATENT DOCUMENTS

| | | |
|---|---|---|
| WO | WO 00/50007 | 8/2000 |
| WO | WO00/66122 | * 11/2000 |
| WO | WO 02/085359 | 10/2002 |
| WO | WO 00/66122 | 11/2002 |

OTHER PUBLICATIONS

U.S. Copending Appl. No. 10/495,425 filed May 21, 2004 and U.S. Appl. No. 10/523,842 filed Feb. 8, 2005.*
Interactions Between Tacrolimus and Antimicrobial Agents; David L. Paterson and Nina Singh; Dec. 1997; pp. 1430-1440.
Effects of Twenty-Three Drugs on The Metabolism of FK506 by Human Liver Microsomes; Kazuhide Iwasaki, Hiroji Matsuda, Kazuko Nagase, Toshifumi Shiraga, Yoji Tokuma, Kazuharu Uchida; Nov. 1993; pp. 209-216.
Norfloxacin interferes with cyclosporine disposition in pediatric patients undergoing renal transplantation; Roman A. McLellan, Robert K. Drobitch, D. Heather McLellan, Philip D. Acott, John F.S. Crocker, Kenneth W. Renton; 1995; pp. 322-327.
Pharmacokinetic Drug Interactions with Antimicrobial Agents; J. Gregory Gillum, Debra S. Israel, Ron E. Polk; 1993; pp. 450-482.
U.S. Appl. No. 10/495,425, filed May 21, 2004, Ueno.
U.S. Appl. No. 10/523,842, filed Feb. 8, 2005, Ueno.

* cited by examiner

*Primary Examiner*—Vickie Kim
(74) *Attorney, Agent, or Firm*—Oblon, Spivak, McClelland, Maier & Neustadt, P.C.

(57) ABSTRACT

The present invention provides a composition for topical administration comprising an interleukin 2 inhibitor and an antimicrobial agent as active ingredients thereof, wherein said interleukin 2 inhibitor contains a tricyclo compound as shown by the general formula (I) or pharmaceutically acceptable salt thereof. The present invention further provides a method for treating inflammations and/or infections comprising topical administration of an effective amount of an interleukin 2 inhibitor and an antimicrobial agent to a subject in need of the treatment of inflammations and/or infections.

14 Claims, No Drawings

COMPOSITION FOR TOPICAL ADMINISTRATION

This application claims benefit of Provisional 60/303,148 filed Jul. 6, 2001.

TECHNICAL FIELD

The present invention relates to a composition for topical administration comprising an interleukin 2 inhibitor and an antimicrobial agent as active ingredients thereof. More particularly, the present invention relates a composition for topical administration comprising an interleukin 2 inhibitor and an antimicrobial agent as active ingredients thereof for the treatment of inflammations and/or infections.

BACKGROUND ART

Interleukin 2 inhibitor is a substance having interleukin 2 inhibitory activity. Known as examples of such substance are interleukin 2 production inhibitory substance and interleukin 2 signal transduction inhibitory substance. Interleukin 2 is necessary for activating T cells to proliferate. Interleukin 2 inhibitor shows an immunosuppressive effect through the T cell activating mechanism.

In recent years, interleukin 2 inhibitors have been tried for the treatment of various inflammations or diseases accompanying inflammations. For example, macrolide compounds such as FK506 and cyclosporins are known to be effective for the treatment of allergic conjunctivitis, allergic dermatitis and allergic rhinitis (U.S. Pat. Nos. 5,514,686, 5,385,907, etc.). Prior to this, the present inventor has reported that interleukin 2 inhibitor(s) comprising macrolide compound(s) such as FK506 are effective for the treatment of dry eye (WO00/66122) and topical ophthalmic treatment of ocular inflammations (U.S. Provisional Application No. 60/283,169, now PCT/JP02/03664).

However, in the topical treatment of various inflammations using interleukin 2 inhibitor, the immunosuppressive effect caused by interleukin 2 inhibitor may result in such side effects as infections. Accordingly, it is desired to develop anti-inflammatory agents reducing such side effects without adversely affecting main effects of interleukin 2 inhibitor.

Meanwhile, antimicrobial agents have been used for the ocular or dermal infection and the prevention of postoperative infection. In treating such infections, it is very important to prevent the proliferation and spread of microorganism at pathologically changed locations. Likewise, it is very important to inhibit the accompanying inflammations or an excessive immuno-inflammatory reaction following phylaxis. In order to meet such requirements, steroid drugs are mainly used as additional anti-inflammatory agents. However, using steroid drugs has the risk of causing such side effects as accentuation of infections by microorganism at pathologically changed locations; thinning of skin and pilosebaceous abnormal activation; weakened vascular wall in the air duct or nasal cavity; and steroidal glaucoma in the eye. Therefore, it is desired to develop safe and effective antimicrobial agent for the treatment of infections and their accompanying inflammations or infections showing an excessive immuno-inflammatory reaction following phylaxis.

DISCLOSURE OF THE INVENTION

The present inventor has conducted intensive studies and found that in the topical treatment of inflammations and/or infections, the combined interleukin 2 (hereinafter, may be simply referred to as IL-2) inhibitor and antimicrobial agent will inhibit inflammations and/or infections without adversely affecting main effects of each agent, which has resulted in the completion of the present invention.

Accordingly, the present invention provides the following.

(1) A composition for topical administration comprising an interleukin 2 inhibitor and an antimicrobial agent as active ingredients thereof.
(2) The composition of (1), wherein said interleukin 2 inhibitor is a macrolide compound or cyclosporins.
(3) The composition of (2), wherein said macrolide compound is a tricyclo compound as shown by the following general formula (I) or pharmaceutically acceptable salt thereof:

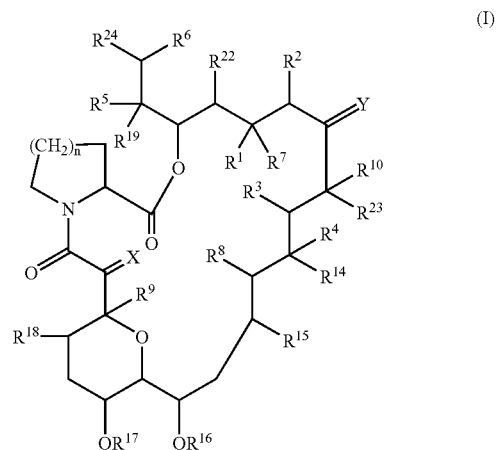

(I)

wherein adjacent pairs of $R^1$ and $R^2$, $R^3$ and $R^4$, and $R^5$ and $R^6$ each independently
a) show two adjacent hydrogen atoms, wherein $R^2$ is optionally alkyl, or
b) form another bond optionally between carbon atoms binding with the members of said pairs;
$R^7$ is hydrogen atom, hydroxy, alkyloxy or protected hydroxy or may form oxo with $R^1$;
$R^8$ and $R^9$ each independently show hydrogen atom or hydroxy;
$R^{10}$ is hydrogen atom, alkyl, alkenyl, alkyl substituted by one or more hydroxy, alkenyl substituted by one or more hydroxy or alkyl substituted by oxo;
X is oxo, (hydrogen atom, hydroxy), (hydrogen atom, hydrogen atom), or a group of the formula —$CH_2O$—;
Y is oxo, (hydrogen atom, hydroxy), (hydrogen atom, hydrogen atom), or a group of the formula N—$NR^{11}R^{12}$ or N—$OR^{13}$;
$R^{11}$ and $R^{12}$ each independently show hydrogen atom, alkyl, aryl or tosyl;
$R^{13}$, $R^{14}$, $R^{15}$, $R^{16}$, $R^{17}$, $R^{18}$, $R^{19}$, $R^{22}$ and $R^{23}$ each independently show hydrogen atom or alkyl;
$R^{24}$ is an optionally substituted ring that may contain one or more heteroatom(s); and
n is 1 or 2;

wherein
Y, $R^{10}$ and $R^{23}$ may show, together with the carbon atom they bind with, a saturated or unsaturated 5 or 6-membered heterocyclic group containing nitrogen atom, sulfur atom and/or oxygen atom, wherein the heterocyclic group may be optionally substituted by one or more group(s) selected from the group consisting of alkyl, hydroxy, alkyloxy, benzyl, a group of the formula —CH$_2$Se(C$_6$H$_5$), and alkyl substituted by one or more hydroxy.

(4) The composition of (3), wherein said tricyclo compound is FK506.

(5) The composition of any of (1) to (4), wherein said antimicrobial agent is quinolone antimicrobial agent.

(6) The composition of (5), wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

(7) The composition of (6), wherein said quinolone antimicrobial agent is ofloxacin.

(8) A method for treating inflammations and/or infections comprising topical administration of an effective amount of an interleukin 2 inhibitor and an effective amount of an antimicrobial agent to a subject in need of the treatment of inflammations and/or infections.

(9) A use of an interleukin 2 inhibitor and an antimicrobial agent for manufacturing a composition for topical administration for the treatment of inflammations and/or infections.

(10) The method of (8), wherein said interleukin 2 inhibitor is a macrolide compound or cyclosporins.

(11) The method of (10), wherein said macrolide compound is a tricyclo compound as shown by the following general formula (I) or pharmaceutically acceptable salt thereof.

(12) The method of (11), wherein said tricyclo compound is FK506.

(13) The method of any of (8) and (10) to (12), wherein said antimicrobial agent is quinolone antimicrobial agent.

(14) The method of (13), wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

(15) The method of (14), wherein said quinolone antimicrobial agent is ofloxacin.

DETAILED DESCRIPTION OF THE INVENTION

The present invention relates to a composition for topical administration comprising an interleukin 2 inhibitor and an antimicrobial agent as active ingredients thereof.

The present invention further relates to a method for treating inflammations and/or infections comprising topical administration of an effective amount of an interleukin 2 inhibitor and an antimicrobial agent to a subject in need of the treatment of inflammations and/or infections.

Moreover, the present invention relates to a use of an interleukin 2 inhibitor and an antimicrobial agent for manufacturing a composition for topical administration for the treatment of inflammations and/or infections.

The present IL-2 inhibitor should not be particularly limited, as far as they have IL-2 inhibitory activity. A specific example of such agents is IL-2 production inhibitory substance. Another specific example of such agent is IL-2 signal transduction inhibitory substance. Preferred specific examples of the above are macrolide compounds (e.g., FK506, ascomycin derivative and rapamycin derivative) and cyclosporins. A single or a combination of two or more IL-2 inhibitors may be used.

The present invention encompasses an embodiment wherein an IL-2 inhibitor and an antimicrobial agent are contained in a single pharmaceutical preparation and an embodiment wherein they are separately formed into pharmaceutical preparations and topically administered simultaneously, which is what is called a combination use.

A specific example of the macrolide compound is a tricyclo compound as shown by the following general formula (I) or pharmaceutically acceptable salt thereof.

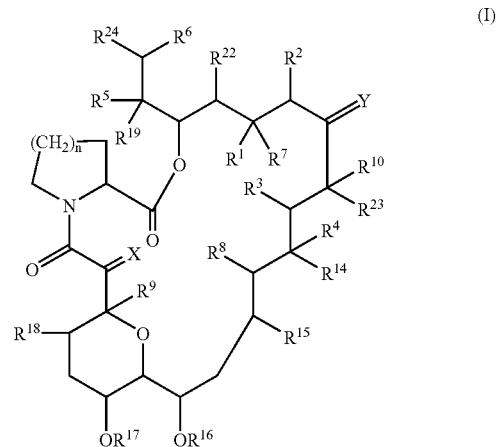

(I)

wherein adjacent pairs of R$^1$ and R$^2$, R$^3$ and R$^4$, and R$^5$ and R$^6$ each independently a) consist of two adjacent hydrogen atoms, wherein R$^2$ is optionally alkyl, or b) form another bond optionally between carbon atoms binding with the members of said pairs;

R$^7$ is hydrogen atom, hydroxy, alkyloxy or protected hydroxy, or may form oxo with R$^1$;

R$^8$ and R$^9$ each independently show hydrogen atom or hydroxy;

R$^{10}$ is hydrogen atom, alkyl, alkenyl, alkyl substituted by one or more hydroxy, alkenyl substituted by one or more hydroxy or alkyl substituted by oxo;

X is oxo, (hydrogen atom, hydroxy), (hydrogen atom, hydrogen atom), or a group of the formula —CH$_2$O—;

Y is oxo, (hydrogen atom, hydroxy), (hydrogen atom, hydrogen atom), or a group of the formula N—NR$^{11}$R$^{12}$ or N—OR$^{13}$;

R$^{11}$ and R$^{12}$ each independently show hydrogen atom, alkyl, aryl or tosyl;

R$^{13}$, R$^{14}$, R$^{15}$, R$^{16}$, R$^{17}$, R$^{18}$, R$^{19}$, R$^{22}$ and R$^{23}$ each independently show hydrogen atom or alkyl;

R$^{24}$ is an optionally substituted ring that may contain one or more heteroatom(s); and n is 1 or 2.

In addition to the meaning noted above, Y, R$^{10}$ and R$^{23}$ may show, together with the carbon atom they bind with, a saturated or unsaturated 5 or 6-membered heterocyclic group containing nitrogen atom, sulfur atom and/or oxygen atom, wherein the heterocyclic group may be optionally substituted by one or more group(s) selected from the group consisting of alkyl, hydroxy, alkyloxy, benzyl, a group of the formula —CH$_2$Se(C$_6$H$_5$), and alkyl substituted by one or more hydroxy, or its pharmaceutically acceptable salt.

In the general formula (I), preferable R$^{24}$ is, for example, cyclo (C$_5$–C$_7$)alkyl optionally having suitable substituent, such as the following.

(a) 3,4-dioxocyclohexyl;
(b) 3-$R^{20}$-4-$R^{21}$-cyclohexyl,
   wherein $R^{20}$ is hydroxy, alkyloxy or —OCH$_2$OCH$_2$CH$_2$OCH$_3$, and
   $R^{21}$ is hydroxy, —OCN, alkyloxy, heteroaryloxy optionally having suitable substituent, —OCH$_2$OCH$_2$CH$_2$OCH$_3$, protected hydroxy, chloro, bromo, iodo, aminooxalyloxy, azide, p-tolyloxythiocarbonyloxy, or $R^{25}R^{26}$CHCOO— (wherein $R^{25}$ is hydroxy optionally protected where desired or protected amino, and $R^{26}$ is hydrogen atom or methyl, or $R^{20}$ and $R^{21}$ in combination form an oxygen atom of epoxide ring); or
(c) cyclopentyl wherein cyclopentyl is substituted by methoxymethyl, optionally protected hydroxymethyl where desired, acyloxymethyl (wherein acyl moiety is optionally quaternized dimethylamino or optionally esterified carboxy), one or more optionally protected amino and/or hydroxy, or aminooxalyloxymethyl.

Preferable examples include 2-formylcyclopentyl.

The definition of each symbol used in the formula (I), specific examples thereof and preferable embodiments thereof will be explained in detail in the following.

"Lower" means a group having 1 to 6 carbon atoms unless otherwise indicated.

Preferable examples of the alkyl moiety of "alkyl" and "alkyloxy" include linear or branched aliphatic hydrocarbon residue, such as lower alkyl (e.g., methyl, ethyl, propyl, isopropyl, butyl, isobutyl, pentyl, neopentyl, hexyl and the like).

Preferable examples of "alkenyl" include linear or branched aliphatic hydrocarbon residue having one double bond, such as lower alkenyl (e.g., vinyl, propenyl (e.g., allyl and the like), butenyl, methylpropenyl, pentenyl, hexenyl and the like).

Preferable examples of "aryl" include phenyl, tolyl, xylyl, cumenyl, mesityl, naphthyl and the like.

Preferable examples of the protective group for "protected hydroxy" and "protected amino" include 1-(loweralkylthio)(lower)alkyl such as lower alkylthiomethyl (e.g., methylthiomethyl, ethylthiomethyl, propylthiomethyl, isopropylthiomethyl, butylthiomethyl, isobutylthiomethyl, hexylthiomethyl and the like), with more preference given to $C_1$–$C_4$ alkylthiomethyl and most preference given to methylthiomethyl;

tri-substituted silyl such as tri(lower)alkylsilyl (e.g., trimethylsilyl, triethylsilyl, tributylsilyl, tert-butyl dimethylsilyl, tri-tert-butylsilyl and the like), and lower alkyldiarylsilyl (e.g., methyldiphenylsilyl, ethyldiphenylsilyl, propyldiphenylsilyl, tert-butyldiphenylsilyl and the like), with more preference given to tri($C_1$–$C_4$)alkylsilyl and $C_1$–$C_4$ alkyldiphenylsilyl, and most preference given to tert-butyl-dimethylsilyl and tert-butyldiphenylsilyl;

acyl such as aliphatic acyl, aromatic acyl and aliphatic acyl substituted by aromatic group, which are derived from carboxylic acid, sulfonic acid and carbamic acid; and the like.

The aliphatic acyl is exemplified by lower alkanoyl optionally having one or more suitable substituent(s) (e.g., carboxy) such as formyl, acetyl, propionyl, butyryl, isobutyryl, valeryl, isovaleryl, pivaloyl, hexanoyl, carboxyacetyl, carboxypropionyl, carboxybutyryl, carboxyhexanoyl and the like;

cyclo(lower)alkyloxy(lower)alkanoyl optionally having one or more suitable substituent(s) (e.g., lower alkyl) such as cyclopropyloxyacetyl, cyclobutyloxypropionyl, cycloheptyloxybutyryl, mentyloxyacetyl, mentyloxypropionyl, mentyloxybutyryl, mentyloxypentanoyl, mentyloxyhexanoyl and the like;

camphorsulfonyl;

lower alkylcarbamoyl having one or more suitable substituent(s) such as carboxy or protected carboxy and the like, such as carboxy(lower)alkylcarbamoyl (e.g., carboxymethylcarbamoyl, carboxyethylcarbamoyl, carboxypropylcarbamoyl, carboxybutylcarbamoyl, carboxypentylcarbamoyl, carboxyhexylcarbamoyl) and tri(lower)alkylsilyl(lower)alkyloxycarbonyl(lower)alkyl-carbamoyl (e.g., trimethylsilylmethoxycarbonylethylcarbamoyl, trimethylsilylethoxycarbonylpropylcarbamoyl, triethylsilylethoxycarbonylpropylcarbamoyl, tert-butyl dimethylsilylethoxycarbonylpropylcarbamoyl, trimethylsilylpropoxycarbonylbutylcarbamoyl); and the like.

Aromatic acyl is exemplified by aroyl optionally having one or more suitable substituent(s) (e.g., nitro), such as benzoyl, toluoyl, xyloyl, naphthoyl, nitrobenzoyl, dinitrobenzoyl, nitronaphthoyl and the like; and arenesulfonyl optionally having one or more suitable substituent(s) (e.g., halogen), such as benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl and the like.

The aliphatic acyl substituted by aromatic group may be, for example, ar(lower)alkanoyl optionally having one or more suitable substituent(s) (e.g., lower alkyloxy or trihalo (lower)alkyl and the like), wherein specific examples are phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl and the like.

Of the above-mentioned acyl, more preferable acyl includes $C_1$–$C_4$ alkanoyl optionally having carboxy, cyclo($C_5$–$C_6$)alkyloxy($C_1$–$C_4$)alkanoyl having two ($C_1$–$C_4$)alkyl in the cycloalkyl moiety, camphorsulfonyl, carboxy ($C_1$–$C_4$) alkylcarbamoyl, tri($C_1$–$C_4$)alkylsilyl($C_1$–$C_4$)alkyloxycarbonyl($C_1$–$C_4$)alkylcarbamoyl, benzoyl optionally having one or two nitro groups, and benzenesulfonyl having halogen, phenyl($C_1$–$C_4$)alkanoyl having $C_1$–$C_4$ alkyloxy and trihalo ($C_1$–$C_4$)alkyl. Of these, most preferred are acetyl, carboxypropionyl, mentyloxyacetyl, camphorsulfonyl, benzoyl, nitrobenzoyl, dinitrobenzoyl, iodobenzenesulfonyl, 2-trifluoromethyl-2-methoxy-2-phenylacetyl and the like.

Preferable, examples of the "heterocyclic group consisting of saturated or unsaturated 5 or 6-membered ring having nitrogen atom, sulfur atom and/or oxygen atom" are pyrrolyl, tetrahydrofuryl and the like.

The "heteroaryl optionally having a suitable substituent" moiety of the "heteroaryloxy optionally having a suitable substituent" is that exemplified for $R^1$ of the compound of the formula I of EP-A-532,088, with preference given to 1-hydroxyethylindol-5-yl. The disclosure is incorporated herein by reference.

The tricyclo compound (I) used in the present invention is described in the publications EP-A-184162, EP-A-323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059 and the like. The disclosures of these publications are incorporated herein by reference.

In particular, the compounds called FR900506 (=FK506), FR900520 (Ascomycin), FR900523 and FR900525 are produced by the genus *Streptomyces*, such as *Streptomyces tsukubaensis*, No. 9993 (depository: National Institute of Advanced Industrial Science and Technology, International Patent Organism Depositary, Central 6, 1—1, Higashi 1-chome, Tsukuba-shi, Ibaraki-ken, Japan (formerly: Fermentation Research Institute, Agency of Industrial Science and Technology, the Ministry of International Trade and Industry), date of deposit: Oct. 5, 1984, deposit number: FERM BP-927) or *Streptomyces hygroscopicus* subsp. *Yakushimaensis*, No. 7238 (depository: National Institute of Advanced Industrial Science and Technology, International Patent Organism Depositary, Central 6, 1—1, Higashi 1-chome, Tsukuba-shi, Ibaraki-ken, Japan (formerly: National Institute of Bioscience and Human-Technology Agency of Industrial Science and Technology, the Ministry of International Trade and Industry), date of deposit: Jan. 12, 1985, deposit number: FERM BP-928 (EP-A-0184162)), and the compound of the following formula, FK506 (general name: Tacrolimus) is a representative compound.

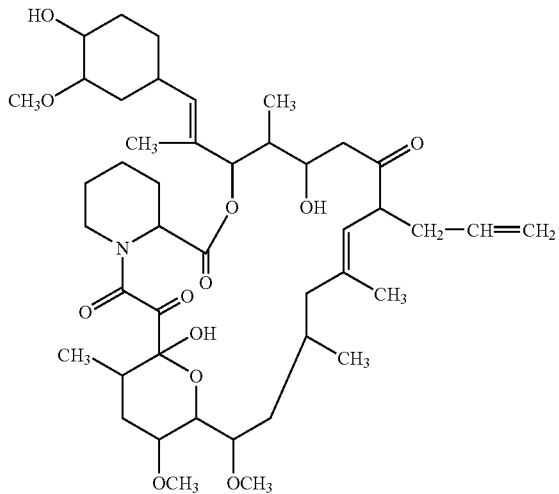

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Of the tricyclo compounds (I), more preferred is a compound wherein adjacent pairs of $R^3$ and $R^4$, and $R^5$ and $R^6$ each independently form another bond optionally between carbon atoms binding with the members of said pairs;

$R^8$ and $R^{23}$ each independently show hydrogen atom;

$R^9$ is hydroxy;

$R^{10}$ is methyl, ethyl, propyl or allyl;

X is (hydrogen atom, hydrogen atom) or oxo;

Y is oxo;

$R^{14}$, $R^{15}$, $R^{16}$, $R^{17}$, $R^{18}$, $R^{19}$ and $R^{22}$ each independently show methyl;

$R^{24}$ is 3-$R^{20}$-4-$R^{21}$-cyclohexyl, wherein $R^{20}$ is hydroxy, alkyloxy or —OCH$_2$OCH$_2$CH$_2$OCH$_3$, and $R^{21}$ is hydroxy, —OCN, alkyloxy, heteroaryloxy optionally having suitable substituent, —OCH$_2$OCH$_2$CH$_2$OCH$_3$, protected hydroxy, chloro, bromo, iodo, aminooxalyloxy, azide, p-tolyloxythiocarbonyloxy or $R^{25}R^{26}$CHCOO— (wherein $R^{25}$ is optionally protected hydroxy as desired, or protected amino, and $R^{26}$ is hydrogen atom or methyl), or $R^{20}$ and $R^{21}$ in combination form an oxygen atom of epoxide ring; and n is 1 or 2.

Particularly preferable tricyclo compounds (I) include, besides FK506, Ascomycin derivatives such as halogenated derivative of 33-epi-chloro-33-desoxy Ascomycin described in Example 66a of EP-A-427,680 and the like.

Other preferable IL-2 inhibitor (macrolide compound) include Rapamycin described in MERCK INDEX, 12 edition, No. 8288 and derivatives thereof. Preferable examples thereof include O-substituted derivative described at page 1 of WO95/16691, formula A, wherein the 40$^{th}$ hydroxy is —OR$_1$ (wherein $R_1$ is hydroxyalkyl, hydroalkyloxyalkyl, acylaminoalkyl and aminoalkyl), such as 40-O-(2-hydroxy)ethyl Rapamycin, 40-O-(3-hydroxy)propyl Rapamycin, 40-O-[2-(2-hydroxy)ethoxy]ethyl Rapamycin and 40-O-(2-acetaminoethyl)-Rapamycin. These O-substituted derivatives can be produced by reacting, under appropriate conditions, Rapamycin (or dihydro or deoxo Rapamycin) and an organic radical bound with leaving group (e.g., RX wherein R is an organic radical desirable as O-substituent, such as alkyl, allyl and benzyl moiety, and X is a leaving group such as CCl$_3$C(NH)O and CF$_3$SO$_3$)). The conditions may be: when X is CCl$_3$C(NH)O, acidic or neutral conditions, such as in the presence of trifluoromethanesulfonic acid, camphorsulfonic acid, p-toluenesulfonic acid or their corresponding pyridinium or substituted pyridinium salt, and when X is CF$_3$SO$_3$, in the presence of a base such as pyridine, substituted pyridine, diisopropylethylamine and pentamethylpiperidine. The most preferable Rapamycin derivative is 40-O-(2-hydroxy)ethyl Rapamycin as disclosed in WO94/09010, which is hereby incorporated into the specification by reference.

The pharmaceutically acceptable salt of tricyclo compound (I), Rapamycin and derivatives thereof are nontoxic and pharmaceutically acceptable conventional salts, which are exemplified by salts with inorganic or organic base such as alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like).

In the IL-2 inhibitor of the present invention, particularly macrolide compound, conformer or one or more pairs of stereoisomers, such as optical isomers and geometric isomers due to asymmetric carbon atom and double bond may be present. Such conformers and isomers are also encompassed in the present invention. In addition, macrolide compounds can form solvates, which case is also encompassed in the present invention. Preferable solvate is exemplified by hydrates and ethanolates.

Other IL-2 inhibitors are known from MERCK INDEX, 12$^{th}$ ed., No. 2821, U.S. Pat. Nos. 4,117,118, 4,215,199, 4,288,431, 4,388,307, Helv. Chim. Acta, 60, 1568 (1977) and 65, 1655 (1982) and Transplant. Proc. 17, 1362 (1985) and the like. Specifically, they are cyclosporins such as cyclosporin A, B, C, D, E, F and G and derivatives thereof. Particularly preferred is cyclosporin A. The disclosures of these publications are incorporated into the specification by reference.

The tricyclo compound (I), pharmaceutically acceptable salt thereof, cyclosporins and derivatives thereof can be classified as "IL-2 production inhibitor" that inhibits production of IL-2. Rapamycin and derivative thereof can be classified as "IL-2 signal transduction inhibitor" that inhibit transmission of IL-2 signal.

The tricyclo compound (I) and its pharmaceutically acceptable salt are nontoxic and pharmaceutically acceptable conventional salts, which are exemplified by salts with inorganic or organic base such as alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like).

In the tricyclo compound of the present invention, conformers or one or more pairs of stereoisomers such as optical isomers and geometric isomers due to asymmetric carbon atom and double bond may be present. Such conformers and isomers are also encompassed in the present invention. In addition, the tricyclo compound can form solvates, which case is also encompassed in the present invention. Examples of preferable solvates include hydrates and ethanolates.

The present antimicrobial agents are not particularly limited, unless they adversely affect the IL-2 inhibitor's inhibitory activity, and preference is given to those antimicrobial agents having no IL-2 inhibitory action. Further preference is given to those antimicrobial agents having a different structure from the macrolide compound (especially the one as shown by the formula (I)) and cyclosporins. Preferred examples of such antimicrobial agents are as follows: penicillins (e.g., benzylpenicillin, methicillin, oxacillin, cloxacillin, ampicillin, hetacillin, carbenicillin, sulbenicillin, bacampicillin, amoxicillin, ticarcillin, piperacillin and aspoxicillin); cephalosporins (e.g., cephalothin, cefazolin, cefotiam, cefotaxime, cefoperazone, ceftizoxime, cefmenoxime, cefpiramide, ceftazidime, cefodizime, cefpiome, cefepime, cefozopran, cefsulodin and cefoselis); cephamycins (e.g., cefoxitin, cefmetazole and cefminox); oxacephems (e.g., latamoxef and flomoxef); monobactams (e.g., aztreonam); carbapenems (e.g., meropenem); penems (e.g., faropenem); aminoglycosides (e.g., amikacin, tobramycin, dibekacin, arbekacin, gentamicin and isepamicin); lincomycins (e.g., lincomycin and clindamycin); tetracyclines (e.g., oxytetracycline, doxycycline and minocycline); chloramphenicols (e.g., chloramphenicol and thiamphenicol); quinolones (nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin); and glycopeptides (e.g., vancomycin and teicoplanin). Preference is given to quinolone antimicrobial agent, with special preference given to ofloxacin. A single or a combination of two or more antimicrobial agents may be used.

The term "treatment" used herein includes any means of control such as prevention, care, relief of the condition, attenuation of the condition and arrest of progression.

The present composition is topically administered to such location as eye, skin, air duct, nasal cavity, labial, pubis and pudenda.

In the case of administering a formulation, the formulation manufactured by conventional methods may be administered, which includes all the formulations for topical ocular administration used in the field of ophthalmology (e.g., eye drops and eye ointment) and all the formulations for external use in the fields of dermatology and otolaryngology (e.g., ointment, cream, lotion and spray).

The eye drops are prepared by dissolving the active ingredient in a sterile aqueous solution such as physiological saline, buffering solution, etc., or by combining powder compositions to be dissolved before use. Eye drops such as the ones as described in EP-A-0406791 are preferred. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, etc.). The disclosure of the above publication is incorporated herein by reference.

The ointment (including eye ointment) is prepared by mixing the active ingredient with the base. The formulation can be prepared according to the ordinary method. For example, mixing the active ingredient into the base ordinarily used for the ointment and formulating it according to ordinary methods can sterily prepare the ointment. Examples of the base for the ointment include petrolatum, selen 50, Plastibase, macrogol, etc., but not limited thereto. Further, in order to increase the hydrophilicity, a surface-active agent can be added. Regarding the ointment, the above-mentioned additives such as the preservatives, etc. can be combined, if necessary.

The present composition can be formulated as a sterile unit dose type containing no preservatives.

The amount of administration and the number of administration of the active ingredient used in the present invention vary according to sex, age and body weight of patient, symptoms to be treated, desirable therapeutic effects, administration routes and period of treatment. Ordinarily, in the case of using as eye drops for an,adult, the formulations containing IL-2 inhibitor of 0.0001–10.0 W/V %, preferably 0.005–5.0 W/V % and the antimicrobial agent of 0.0001–50.0 W/V %, preferably 0.005–10.0 W/V % may be administered several times a day per eye, preferably one to six times, more preferably one to four times, several drops per time, preferably one to four drops. In using for ointment, cream, lotion or spray, the formulations containing IL-2 inhibitor of 0.0001–10.0 W/V %, preferably 0.005–5.0 W/V % and the antimicrobial agent of 0.0001–50.0 W/V %, preferably 0.005–10.0 W/V % may be applied or sprayed several times a day, preferably one to six times, more preferably one to four times. The compounding ratio of each ingredient may be suitably increased or decreased based on the degree of inflammations or infections.

In the present invention, the formulation can include a single IL-2 inhibitor and antimicrobial agent as active ingredients thereof or a combination of two or more of these agents. In a combination of plural active ingredients, their respective contents may be suitably increased or decreased in consideration of their effects and safety.

When an IL-2 inhibitor and an antimicrobial agent are separately formed into pharmaceutical preparations and topically administered simultaneously according to the present invention, the dose of the active ingredient and administration frequency can be appropriately determined in consideration of sex, age and body weight of patient, symptoms to be treated, desirable therapeutic effects, administration routes and period of treatment.

The present formulation can further include other pharmacological active ingredients as far as they do not contradict the purpose of the present invention.

The inflammations and/or infections in the present invention are not particularly limited, as far as they are the diseases topically treated at eye, skin, air duct, nasal cavity, labial, pubis, pudenda, etc. Examples of such diseases are as follows: infections caused by microorganism such as bacteria (e.g., *Staphylococcus aureus, Pseudomonas aeruginosa, Streptococcus, gonococcus* and Syphilis) and fungi (trichophyton, *Malassezia* and *Candida*); diseases generically called dermatitis such as allergic dermatitis (e.g., atopic dermatitis and contact dermatitis) and dermatitis seborrheica; diseases accompanying ocular inflammations such as uveitis, conjunctivitis, cyclitis, scleritis, episcleritis, optic neuritis, retrobulbar optic neuritis, keratitis, blepharitis, corneal ulcer and conjunctival ulcer; diseases generically called rhinitis such as allergic rhinitis and vasomoter rhinitis; diseases accompanying air duct inflammations such as bronchial asthma, infantile asthma, acute bronchitis and chronic bronchitis. The present invention also includes inflammations and/or infections at locations undergoing ophthalmic operations (e.g., operation for cataract) or surgical operations.

The present invention enables to inhibit inflammations and/or infections by topically treating with a combination of interleukin 2 inhibitor and antimicrobial agent without adversely affecting main effects of each ingredient. The present invention also enables to reduce the dosage of active ingredients, as compared with a single use of each ingredient, and to obtain strong anti-inflammatory and/or antimicrobiral activities with a small dosage, thus providing a drug with reduced side effects. Accordingly, the present composition may be effectively and safely administered for the treatment of infections and their accompanying inflammations or infections of a subject showing the excessive immuno-inflammatory reaction following phylaxis. Further, the present composition may be effectively and safely administered for the treatment of inflammations of a subject showing signs of infections or spreading infections due to the immunosuppressant effect caused by IL-2 inhibitor or some causes (injuries or operation) other than IL-2 inhibitor.

The present invention will be described in more detail with reference to the following examples, which are not intended to limit the present invention.

EXAMPLE 1

A pharmaceutical composition for topical treatment of the present invention was prepared.

EXAMPLE 1

| FK-506 | 0.3 mg | 0.03% |
|---|---|---|
| ofloxacin | 3 mg | 0.3% |
| Benzalkonium Chloride | 0.1 mg | 0.01% |
| Sodium Chloride | 8.56 mg | 0.856% |
| Disodium hydrogen phosphate | 0.05 mg | 0.005% |
| Sodium dihydrogen phosphate | 0.76 mg | 0.076% |
| Phosphoric acid and/or Sodium Hydroxide | q.s. for pH adjustment to 5.0 ± 0.5 | |
| Purified Water | q.s. to 1 mL | q.s. to 100% |

TEST EXAMPLE 1 (ANTI-MICROBIAL TEST)

Single colony isolate of *Pseudomonas aeruginosa* IID-1210 (provided by Department of Ophthalmology, Yokohama City University School of Medicine, Japan) on NAC agar plate was inoculated in 2 mL of heart infusion broth, and kept for overnight at 37° C. One hundred microliters of the overnight culture was inoculated in 10 mL of heart infusion broth, and then grown for about 12 hours at 37° C. with shaking.

Twelve Japanese white rabbits (13 weeks old, Std: JW/CSK, Japan SLC, Inc.) were anesthetized by intravenous injection of pentobarbital sodium (25 mg/kg), and then topical anesthesia was made by instillation of 0.4% oxybuprocaine hydrochloride to both eyes. The corneal wound was produced bilaterally using a 6-mm trephine and 27-gauge needle according to the method described by Hatano H et al. (Japanese Review of Clinical Ophthalmology 79: 1153, 1985). Forty microliters of the bacterial suspension prepared above was instilled onto the wounded cornea twice (Day 1, 21:00). After bacterial inoculation, the rabbits were divided into 4 groups (three rabbits-six eyes/group). Fifty microliters of each test substance or vehicle was topically applied to both eyes of each animal once 12 hours after bacterial inoculation (Day 2, 9:00).

As test substances, 0.06% FK-506 (group 2), 0.03% ofloxacin (group 3), a mixture containing 0.06% FK-506 and 0.03% ofloxacin (group 4) and a vehicle (group 1) were used.

Four hours after administration of test substances, the animals were sacrificed with an intravenous overdose of pentobarbital sodium, eyes were enucleated, and then corneas were excised using a 6-mm trephine. After weighing, each cornea was homogenized in 1 mL of sterile physiological saline. Aliquot (0.1 mL) of each homogenate was plated on NAC agar, and incubated for 24 hours at 37° C. The colonies were then counted. All quantitative cultures were run in triplicate, and the arithmetic mean of three measurements was determined for each cornea. Results were expressed as the number of organisms (determined by measures of colony forming units [CFU]) per gram of corneal weight.

Table 1 shows the colony forming units of each group. Treatment with 0.06% FK-506 decreased the viable Pseudomonas counts as compared with vehicle treatment, but not significantly. Treatment with 0.3% ofloxacin eradicated the bacteria. Treatment with mixture containing 0.06% FK-506 and 0.3% ofloxacin also eradicated the bacteria. The results indicated that FK-506 had no effect on the inhibition of infection by ofloxacin.

It has been also clarified that a combined use with an antimicrobial agent, such as ofloxacin, obviates the risk of bacterial infection associated with single administration of an IL-2 inhibitor having an immunosuppressive action, such as FK-506.

TABLE 1

| Group | Treatment | Number of eyes | Colony forming units per gram of cornea Mean ± SE |
|---|---|---|---|
| 1. | Vehicle (Control) | 6 | 43382 ± 16081 |
| 2. | 0.06% FK-506 | 6 | 31225 ± 7204 |
| 3. | 0.3% ofloxacin | 6 | 0[a),b)] |
| 4. | 0.06% FK-506 0.3% ofloxacin | 6 | 0[a),b)] |

[a)] $p < 0.05$ Significantly different from group 1 (Tukey test)
[b)] $p < 0.01$ Significantly different from group 2 (Tukey test)

TEST EXAMPLE 2 (ANTI-INFLAMMATORY TEST)

Experimental *Pseudomonas keratitis* was induced for 12 Japanese white rabbits (13 weeks old, Std: JW/CSK) as described in Test Experiment 1. After bacterial inoculation, the rabbits were divided into 4 groups (three rabbits-six eyes/group). Fifty microliters of each test substance or vehicle was topically applied to both eyes of each animal 4 times a day at intervals of 4 hours beginning 12 hours after the bacterial inoculation. The test substance and vehicle were the same as those used in Test Example 1.

Rabbit eyes were examined with a slit lamp biomicroscope, and severity of conjunctival inflammation at 48 hours after bacterial inoculation and corneal inflammation at 60 hours after bacterial inoculation were evaluated by assigning a numerical value to the following signs based on the method described by Kuriyama H et al. Corneal inflammation was evaluated by sums of the scores of corneal opacity (score 0–8) and corneal ulcer (score 0–3). Conjunctival inflammation was evaluated by sums of the scores of redness of palpebral conjunctival inflammation (score 0–4), edema of palpebral conjunctiva (score 0–4), nictitating membrane status (score 0–3) and discharge (score 0–3).

As shown in Table 2, the treatment with 0.06% FK-506 or 0.3% ofloxacin tended to decrease the conjunctival inflammation. Treatment with the mixture containing 0.06% FK-506 and 0.3% ofloxacin decreased significantly the conjunctival inflammation as compared with vehicle treatment.

TABLE 2

| Group | Treatment | Number of eyes | Score (conjunctiva) Mean ± SE |
|---|---|---|---|
| 1. | Vehicle (Control) | 6 | 7.3 ± 0.6 |
| 2. | 0.06% FK-506 | 6 | 6.7 ± 0.4 |
| 3. | 0.3% ofloxacin | 6 | 6.0 ± 0.5 |
| 4. | 0.06% FK-506 0.3% ofloxacin | 6 | 5.5 ± 0.3[a)] |

[a)]$p < 0.05$ Significantly different from group 1 (Tukey test)

As shown in Table 3, treatments with 0.06% FK-506 tended to decrease the corneal inflammation. Treatment with 0.3% ofloxacin or the mixture containing 0.06% FK-506 and 0.3% ofloxacin decreased significantly the corneal inflammation as compared with vehicle treatment. The mixture containing 0.06% FK-506 and 0.3% ofloxacin decreased significantly the corneal inflammation as compared with 0.06% FK-506 treatment.

TABLE 3

| Group | Treatment | Number of eyes | Score (cornea) Mean ± SE |
|---|---|---|---|
| 1. | Vehicle (Control) | 6 | 7.3 ± 1.0 |
| 2. | 0.06% FK-506 | 6 | 6.0 ± 0.0 |
| 3. | 0.3% ofloxacin | 6 | 2.1 ± 0.4[a)] |
| 4. | 0.06% FK-506 0.3% ofloxacin | 6 | 1.6 ± 0.3[a),b)] |

[a)]$p < 0.01$ Significantly different from group 1 (Tukey test)
[b)]$p < 0.05$ Significantly different from group 2 (Tukey test)

The above results indicated that topical treatment with a combination of FK-506 and ofloxacin inhibited inflammation and/or infection without adversely affecting main effects of each ingredient. The results further indicate that FK-506 and ofloxacin showed an addictive effect and/or synergistic effect on inflammation when used in combination.

INDUSTRIAL APPLICABILITY

A composition for topical administration comprising an interleukin 2 inhibitor and an antimicrobial agent as active ingredients shows an antiinflammatory effect while suppressing side effects, such as infectious diseases and the like. The composition for topical administration of the present invention affords prevention or treatment of infectious diseases, therewith-associated inflammation or infectious diseases accompanying excessive immunoinflammatory response due to phylaxis, while suppressing inflammation. Therefore, the composition for topical administration of the present invention is useful for the treatment of inflammation and/or infectious diseases.

This application is based on application No. 60/303,148 filed in United States of America, the content of which is incorporated hereinto by reference.

What is claimed is:
1. An ophthalmic composition for ocular administration comprising active ingredients, and wherein the active ingredients consist of an interleukin 2 inhibitor and an antimicrobial agent, and
wherein the interleukin 2 inhibitor is a tricyclo compound as shown by the following general formula (I) or pharmaceutically acceptable salt thereof:

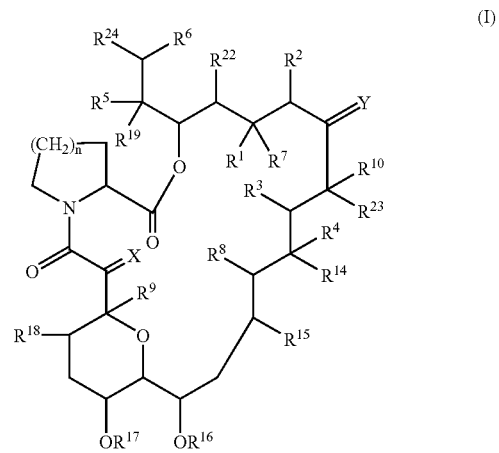

wherein adjacent pairs of $R^1$ and $R^2$, $R^3$ and $R^4$, and $R^5$ and $R^6$ each independently
a) are two adjacent hydrogen atoms, wherein $R^2$ is optionally alkyl, or
b) form another bond optionally between carbon atoms binding with the members of said pairs;
$R^7$ is hydrogen atom, hydroxy, alkyloxy or protected hydroxy or may form oxo with $R^1$;
$R^8$ and $R^9$ each independently are hydrogen atom or hydroxy;
$R^{10}$ is hydrogen atom, alkyl, alkenyl, alkyl substituted by one or more hydroxy, alkenyl substituted by one or more hydroxy or alkyl substituted by oxo;
X is oxo;
Y is oxo, (hydrogen atom, hydroxy), (hydrogen atom, hydrogen atom), or a group of the formula N—NR$^{11}$R$^{12}$ or N—OR$^{13}$;
$R^{11}$ and $R^{12}$ each independently are hydrogen atom, alkyl, aryl or tosyl;
$R^{13}$, $R^{14}$, $R^{15}$, $R^{16}$, $R^{17}$, $R^{18}$, $R^{19}$, $R^{22}$ and $R^{23}$ each independently are hydrogen atom or alkyl; $R^{24}$ is an optionally substituted ring that may contain one or more heteroatom(s); and n is 1 or 2;
wherein Y, $R^{10}$ and $R^{23}$ may show, together with the carbon atom they bind with, a saturated or unsaturated 5 or 6-membered heterocyclic group containing nitrogen atom, sulfur atom and/or oxygen atom, wherein the heterocyclic group may be optionally substituted by one or more group(s) selected from the group consisting of alkyl, hydroxy, alkyloxy, benzyl, a group of the formula —CH$_2$Se(C$_6$H$_5$), and alkyl substituted by one or more hydroxyl; and wherein the antimicrobial agent is a quinolone antimicrobial agent.

2. The composition of claim 1, wherein said interleukin 2 inhibitor is FK506.

3. The composition of claim 1, wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

4. The composition of claim 3, wherein said quinolone antimicrobial agent is ofloxacin.

5. A method for treating ocular inflammations and/or ocular infections comprising, topical administration of an effective amount of the ophthalmic composition according to claim 1, to a subject in need thereof.

6. The method of claim 5, wherein said interleukin 2 inhibitor is FK506.

7. The method of claim 5, wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

8. The method of claim 7, wherein said quinolone antimicrobial agent is ofloxacin.

9. An ophthalmic composition for ocular administration, comprising active ingredients and a topically acceptable carrier, wherein the active ingredients of the composition consist essentially of FK506 and a quinolone antimicrobial agent.

10. The composition of claim 9, wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

11. The composition of claim 10, wherein said quinolone antimicrobial agent is ofloxacin.

12. A method for treating ocular inflammations and/or ocular infections comprising topical administration of an ophthalmic composition to a subject in need of the treatment of ocular inflammations and/or ocular infections, wherein the composition contains active ingredients consisting essentially of an effective amount of FK506 and an effective amount of a quinolone antimicrobial agent.

13. The method of claim 12, wherein said quinolone antimicrobial agent is nalidixic acid, pipemidic acid, piromidic acid, norfloxacin, ofloxacin, levofloxacin, ciprofloxacin, lomefloxacin, tosufloxacin, fleroxacin, sparfloxacin, enrofloxacin and enoxacin or a mixture thereof.

14. The method of claim 13, wherein said quinolone antimicrobial agent is ofloxacin.

* * * * *